Figure 1:
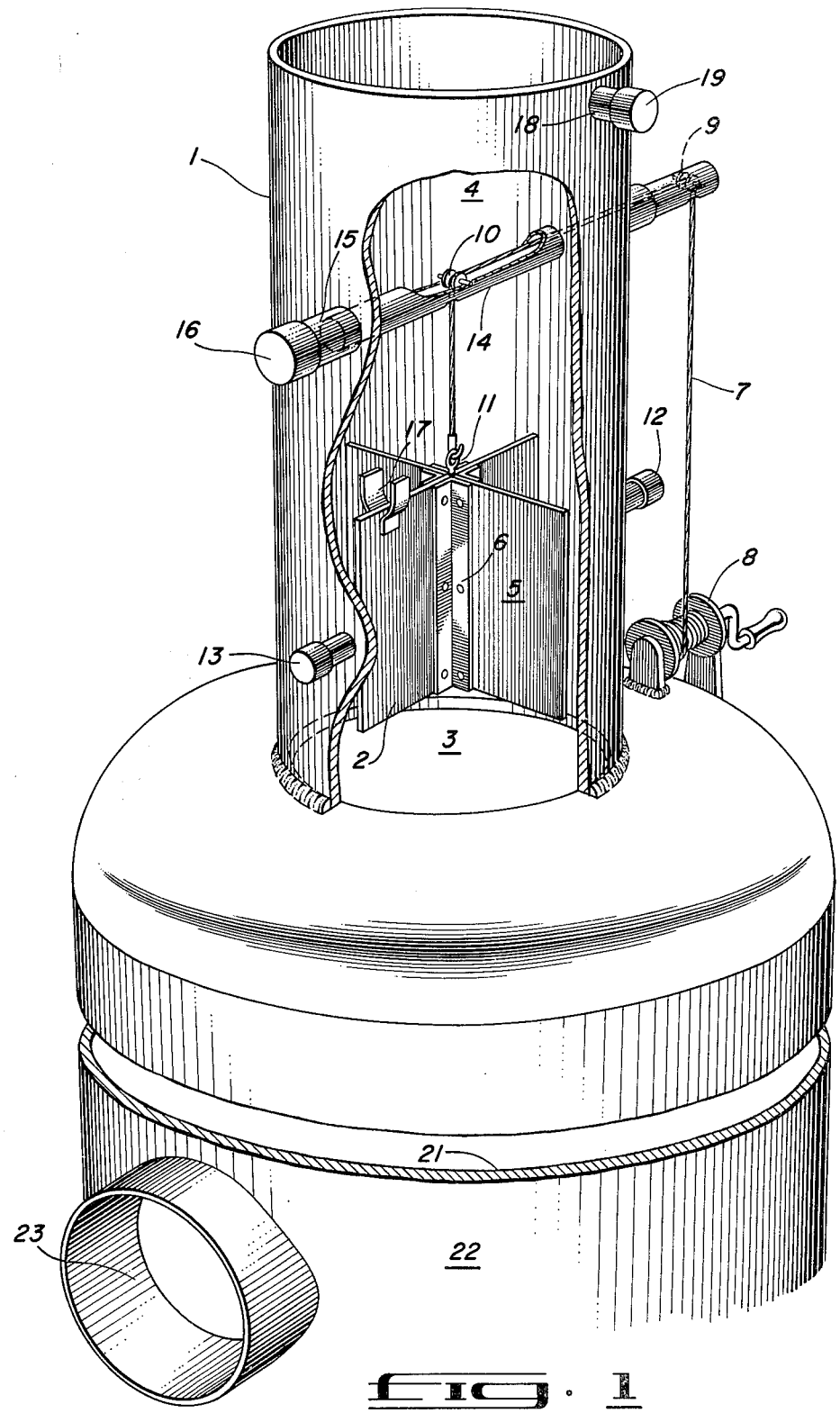
Figure 2:
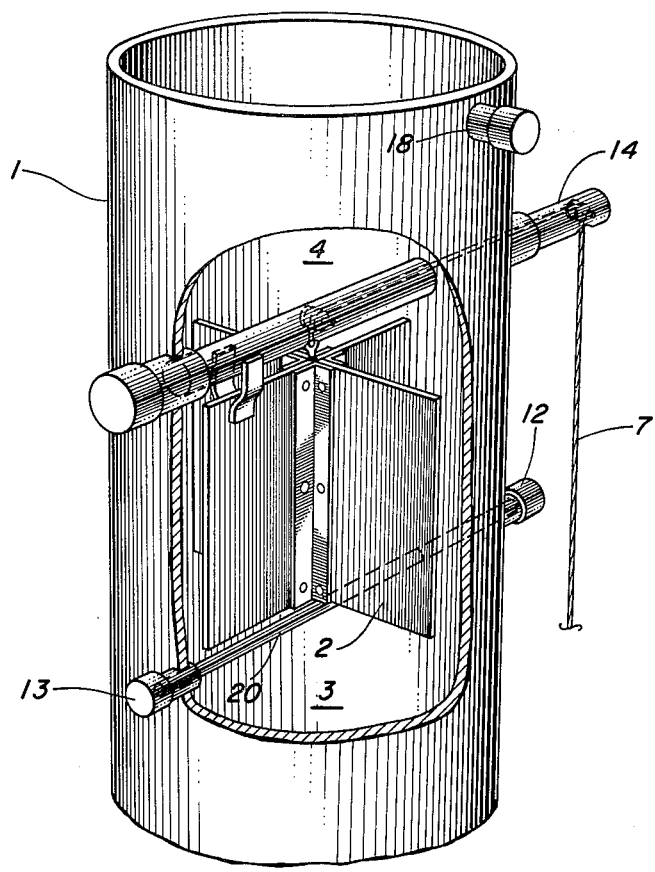

United States Patent [19]

Smith et al.

[11] 4,422,342

[45] Dec. 27, 1983

[54] TEMPORARY VANES TO STRAIGHTEN GAS FLOW IN SCRUBBERS

[75] Inventors: Donald L. Smith, Bethel Park; Zenon V. Kosowski, McMurray, both of Pa.; Robert R. Marks, Jr., Fairmont, W. Va.

[73] Assignee: Conoco Inc., Wilmington, Del.

[21] Appl. No.: 358,126

[22] Filed: Mar. 15, 1982

[51] Int. Cl.³ ............................................. G01N 1/22
[52] U.S. Cl. ................................. 73/863.43; 55/416; 138/37; 138/39
[58] Field of Search ................ 55/415, 416, 220, 270; 261/96, 109; 73/863.41, 863.43; 138/37, 39

[56] References Cited

U.S. PATENT DOCUMENTS 3,343,341  9/1967  Wiemar .................................. 55/415
3,546,851 12/1970  Hardison et al. ...................... 55/416
3,842,678 10/1974  De Baun et al. ................... 73/863.43

FOREIGN PATENT DOCUMENTS 29383 of 1911  United Kingdom .................. 55/415

Primary Examiner—S. Clement Swisher
Assistant Examiner—John E. Chapman, Jr.
Attorney, Agent, or Firm—Dale Lovercheck; William A. Mikesell, Jr.

[57] ABSTRACT

A method is provided for flow straightening and sampling gas in the stack of a gas scrubber. In normal operation the gas has a substantially nonaxial flow so as to retain within the stack droplets carried by the gas. A flow straightener having flow straightening panels is assembled in the chamber of the gas scrubber and lifted into the stack. Gas having an axial flow is then sampled. The flow straightener is then removed from the scrubber, and normal operation is resumed.

5 Claims, 2 Drawing Figures

TEMPORARY VANES TO STRAIGHTEN GAS FLOW IN SCRUBBERS

BACKGROUND OF THE INVENTION

The invention relates to the sampling of gas above a scrubber. These samples are used to determine the particulate concentration in the gas leaving the scrubbers. When permanent straightening vanes are used in scrubber stacks, laminar gas flow occurs resulting in droplets being carried out of the stack. These droplets might otherwise impact the walls and flow out with the scrubber effluent. The methods for sampling particulate cannot distinguish between dust and other particles in a gas stream and dust in the slurry droplets. This may result in sampling results being biased high. The removal of the flow straightening device allows the swirling of the gases to impact the droplets upon the stack wall. The slurry is thus contained within the scrubber.

The present invention provides a method for the installation of temporary vanes which when installed provide axial gas flow ideal for the sampling of particulate. Because the vanes are removed during normal operation, the amount of droplets leaving the top of the stack is significantly reduced. This eliminates dirty rain from the stack, a pollution hazard itself. More importantly, the few droplets which are carried out of the stack are substantially without any solids in them as compared with the significant amount of dust in such particles where the straightening vanes are permanently installed.

SUMMARY OF THE INVENTION

A method of sampling stack gas from a scrubber stack comprises providing a flow straightener in the chamber of a scrubber having a scrubber stack and a scrubber chamber, said flow straightener comprising a plurality of flow straightening panels and a flow straightening panel support means, providing upper lifting support means, lifting said flow straightener from said scrubber chamber into said scrubber stack while said flow straightener is supported by said upper lifting support means, sampling gas in said stack, lowering said flow straightener into said scrubber chamber.

BRIEF DESCRIPTION OF THE DRAWINGS

FIG. 1 shows the installation of a flow straightener in accordance with the present invention.

FIG. 2 shows the flow straightener in its operating position.

DETAILED DESCRIPTION OF THE DRAWINGS

With more particular reference to the Figures, the invention provides for the sampling of gas in a scrubber stack, coupled with the ease of installing and removing the vanes. FIG. 1 shows a scrubber stack 1 above a flow straightener 2. The scrubber stack 1 has lower scrubber stack chamber 3 wherein the flow of gas therethrough is nonaxial. The scrubber stack 1 has upper scrubber stack chamber 4 wherein the gaseous flow more closely approximates axial flow than the gas flow in the lower scrubber stack chamber 3.

Below the scrubber stack 1 is a gas scrubber 22 defined by scrubber chamber wall 21. Gas scrubbers are provided with manholes through which operators may enter and leave the scrubber chamber. In carrying out the method of the present invention, a flow straightener is brought into the scrubber chamber in separate panels through manhole 23. These panels are the flow straightener panels 5. The flow straightener panels 5 are fixed to the flow straightener panel support 6 in the scrubber chamber 22. By providing a winch 8 and a lifting cable 7, the flow straightener 2 is lifted from the scrubber chamber by the lifting cable 7. The lifting cable 7 is supported by the lifting bar 14, the lifting bar 14 is provided with outer lifting pulley 9 and center lifting pulley 10 both of which serve to guide the lifting cable 7. The flow straightener 2 is attached to the lifting cable 7 by the lifting cable fastener 11. The flow straightener 2 is lifted to a position below the lifting bar 14 and above the safety support port 12. The safety support port 12 is provided with a safety support port cap 13. By removing the safety support port cap 13 and inserting a safety support bar 20, as shown in FIG. 2, the flow straightener is prevented from falling through the scrubber stack 1 if the lifting cable breaks.

By lifting the flow straightener close enough to the lifting bar 14, the anti-rotation tabs 17 may be positioned on either side of the lifting bar to prevent rotation of the flow straightener.

During sampling, the scrubber is operated and the gas from the scrubber passes past the flow straightener 2 which provides that gas with a flow pattern which is of a more axial nature. By removing the sampling port cap 19 from the sampling port 18, the cross section of the upper scrubber stack chamber 4 may be sampled for gas samples.

After the sampling is completed, the sampling port cap 19 is placed back over the sampling port 18. The flow straightener is lowered back into the scrubber chamber below the scrubber stack 1. The lifting bar 14 is removed from the lifting ports 15 and the lifting caps 16 are placed over the lifting ports 15. Of course, prior to lowering the flow straightener 2, the safety support bar 20 is removed from the safety support ports 12 and the safety support port caps 13 are placed over the safety support ports 12.

The flow straightener is disassembled in the scrubber chamber 22 and removed through the scrubber chamber manhole 23.

Having thus described the invention by reference to certain of its preferred embodiments it is respectfully pointed out that embodiments described are illustrative rather than limiting in nature and that many variations and modifications are possible within the scope of the present invention. Such variations and modifications may appear obvious and desirable to those skilled in the art upon a review of the foregoing description of preferred embodiments.

Having described our invention we claim:

1. A method of flow straightening and sampling gas in the stack of a gas scrubber said gas during normal operation of the scrubber having substantially nonaxial flow so as to retain within said stack droplets carried by said gas, comprising the sequence of steps as follows:

(a) providing a plurality of flow straightening panels and a flow straightening panel support means in the chamber of the gas scrubber, said panels connected to said panel support means to form a flow straightener, (b) providing upper lifting support means to support said flow straightener, (c) lifting said flow straightener from said scrubber chamber into said scrubber stack using said lifting support means, (d) providing said flow straightener with a lower safety support means to support said flow straightener in said stack, (e) conveying gas through said scrubber stack and through said flow straightener, whereby said gas flow is straightened to more closely approximate axial flow, (f) sampling gas in said stack after said gas has passed through said flow straightener, (g) removing said safety support means and lowering said flow straightener into said scrubber chamber, (h) disconnecting said panels from said panel support means and removing said panels and panel support means from said scrubber chamber, (i) conveying gas through said scrubber stack in substantially droplet retaining nonaxial flow.

2. The method of claim 1 wherein said upper lifting support means comprises a lifting bar.

3. The method of claim 2 wherein said upper lifting support means further comprises a lifting cable.

4. The method of claim 1 wherein said lower safety support means comprises a safety support bar positioned beneath said flow straightener.

5. The method of claim 1 wherein said flow straightener is provided with at least two anti-rotation tabs to prevent said flow straightener from rotating in said stack.

* * * * *